(12) United States Patent
Mehta

(10) Patent No.: US 10,443,095 B2
(45) Date of Patent: Oct. 15, 2019

(54) HELPER OLIGONUCLEOTIDE FOR IMPROVED EFFICIENCY OF AMPLIFICATION AND DETECTION/QUANTITATION OF NUCLEIC ACIDS

(71) Applicant: Roche Molecular Systems, Inc., Pleasanton, CA (US)

(72) Inventor: Rochak Mehta, Fremont, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 68 days.

(21) Appl. No.: 15/660,686

(22) Filed: Jul. 26, 2017

(65) Prior Publication Data

US 2018/0037945 A1 Feb. 8, 2018

Related U.S. Application Data

(60) Provisional application No. 62/370,049, filed on Aug. 2, 2016.

(51) Int. Cl.

| *C12Q 1/68* | (2018.01) |
| *C12Q 1/6848* | (2018.01) |
| *C12Q 1/686* | (2018.01) |
| *C12Q 1/689* | (2018.01) |
| *C12Q 1/70* | (2006.01) |
| *C12Q 1/6844* | (2018.01) |

(52) U.S. Cl.
CPC ........... *C12Q 1/6848* (2013.01); *C12Q 1/686* (2013.01); *C12Q 1/689* (2013.01); *C12Q 1/6844* (2013.01); *C12Q 1/707* (2013.01)

(58) Field of Classification Search
None
See application file for complete search history.

(56) References Cited

U.S. PATENT DOCUMENTS

| 5,210,015 A | 5/1993 | Gelfand et al. |
| 5,487,972 A | 1/1996 | Gelfand et al. |
| 5,882,852 A * | 3/1999 | Bukh .................. C07K 14/005 435/5 |
| 9,447,476 B2 | 9/2016 | Babiel et al. |
| 2003/0008274 A1 * | 1/2003 | Maertens ............. C07K 14/005 435/5 |
| 2004/0110182 A1 | 6/2004 | Koizumi et al. |
| 2009/0017070 A1 * | 1/2009 | Liang ...................... C12N 7/00 424/228.1 |
| 2010/0261154 A1 | 10/2010 | Esping et al. |
| 2011/0282043 A1 | 11/2011 | Dubois |
| 2011/0300544 A1 | 12/2011 | Fu |
| 2013/0280697 A1 * | 10/2013 | Leying .................. C12Q 1/707 435/5 |

FOREIGN PATENT DOCUMENTS

| CN | 105483283 A | 4/2016 | |
| WO | WO-9425601 A2 * | 11/1994 | ........... C07K 14/005 |
| WO | 1995/013399 A1 | 5/1995 | |
| WO | WO-9605315 A2 * | 2/1996 | ........... C07K 14/005 |
| WO | 2001/094638 A2 | 12/2001 | |
| WO | 2003/062445 A2 | 7/2003 | |
| WO | 2006/135765 A1 | 12/2006 | |
| WO | 2008064687 A1 | 6/2008 | |
| WO | WO-2008141651 A1 * | 11/2008 | ........... C07K 14/005 |
| WO | 2009043112 A1 | 4/2009 | |
| WO | 2015185655 A1 | 12/2015 | |

OTHER PUBLICATIONS

International Searching Authority, Notification of Transmittal of International Search Report and the Written Opinion of the International Searching Authority, or the Declaration for International Patent Application PCT/EP2017/068839 (dated Oct. 6, 2017).
Roche Molecular Diagnostics, cobas HCV GT: HCV genotyping test for use on the cobas 4800 System (2016).

\* cited by examiner

*Primary Examiner* — Samuel C Woolwine
(74) *Attorney, Agent, or Firm* — Eric Grant Lee

(57) ABSTRACT

Improved methods for the detection and quantitation of a target nucleic acid in a sample using a non-extending helper oligonucleotide are described. The methods include contacting nucleic acids in a sample with amplification reagents including one or more primers, one or more non-extending helper oligonucleotides, and one or more probes. The non-extending helper oligonucleotide facilitates and increases the target nucleic acid accessibility of one or more of the primers, result in greater accumulation of amplicon production, thereby increasing the efficiency and sensitivity of the amplification assay, including amplification assays for Hepatitis C Virus (HCV), for example, HCV Genotype 5. Kits, articles of manufacture, and reaction mixtures are also provided.

6 Claims, 4 Drawing Sheets
Specification includes a Sequence Listing.

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Forward Primer
<220> FEATURE:
<221> NAME/KEY: modified_base
<222> LOCATION: (18)..(18)
<223> OTHER INFORMATION: t-Butyl Benzyl-dC

<400> SEQUENCE: 1
tgggcagggt ggttgctc                                                 18

<210> SEQ ID NO 2
<211> LENGTH: 25
<212> TYPE: DNA
<213> ORGANISM: Artificial Sequence
<220> FEATURE:
<223> OTHER INFORMATION: Reverse Primer
<220> FEATURE:
<221> NAME/KEY: modified_base
<222> LOCATION: (25)..(25)
<223> OTHER INFORMATION: t-Butyl Benzyl-dA

<400> SEQUENCE: 2
gttgcatagt ttaccccgtc ctcaa                                         25

<210> SEQ ID NO 3
<211> LENGTH: 25
<212> TYPE: DNA
<213> ORGANISM: Artificial Sequence
<220> FEATURE:
<223> OTHER INFORMATION: Reverse Primer
<220> FEATURE:
<221> NAME/KEY: modified_base
<222> LOCATION: (25)..(25)
<223> OTHER INFORMATION: t-Butyl Benzyl-dA

<400> SEQUENCE: 3
gttgcatagt ttatcccgtc ctcaa                                         25

<210> SEQ ID NO 4
<211> LENGTH: 25
<212> TYPE: DNA
<213> ORGANISM: Artificial Sequence
<220> FEATURE:
<223> OTHER INFORMATION: Probe

<400> SEQUENCE: 4
atcccgctcg taggcggccc cgttg                                         25

<210> SEQ ID NO 5
<211> LENGTH: 53
<212> TYPE: DNA
<213> ORGANISM: Artificial Sequence
<220> FEATURE:
<223> OTHER INFORMATION: Non-Extending Helper Oligonucleotide
```

```
<400> SEQUENCE: 5
gttgcatagt ttatcccgtc ttcaagaacc ttcacaccgt gtgcgaaaaa aaa          53
```

HELPER OLIGONUCLEOTIDE FOR IMPROVED EFFICIENCY OF AMPLIFICATION AND DETECTION/QUANTITATION OF NUCLEIC ACIDS

CROSS REFERENCE TO RELATED APPLICATIONS

This application claims the benefit of priority of U.S. Provisional Patent Application No. 62/370,049, filed Aug. 2, 2016, which is incorporated herein by reference in its entirety.

FIELD OF THE INVENTION

The present disclosure relates to the field of in vitro diagnostics. Within this field, the present invention is directed to improved methods for the detection of a target nucleic acid that may be present in a sample (e.g., biological or non-biological sample). In particular, the present invention concerns the detection and quantitation of a target nucleic acid, with the aid or help of a non-extending helper oligonucleotide that enhances the activity of the primers. By enhancing the activity of the primers, the non-extending helper oligonucleotide improves amplification efficiency, which results in greater and enhanced amplicon production. The improvement, therefore, allows for a more efficient and more sensitive detection and quantitation method. The invention further provides reaction mixtures and kits containing the non-extending helper oligonucleotide, primers, and probes for detection and quantitation target nucleic acid that may be present in a sample. This present invention is useful, for example, for the detection and quantitation of viral or bacterial nucleic acid in samples.

BACKGROUND OF THE INVENTION

In the field of molecular diagnostics, the amplification and detection/quantitation of nucleic acids is of considerable significance and importance. Examples for diagnostic applications of nucleic acid amplification and detection are for the detection and amplification of microbial nucleic acids. Such microbial nucleic acids may include bacterial nucleic acids and/or viral nucleic acids. The amplification and detection/quantitation techniques are suitable for viral nucleic acid targets, such as Human Papilloma Virus (HPV) or West Nile Virus (WNV), or the routine screening of blood donations for the presence of Human Immunodeficiency Virus (HIV), Hepatitis A Virus (HAV), Hepatitis B Virus (HBV), or Hepatitis C Virus (HCV). The amplification and detection/quantitation techniques are also suitable for bacterial nucleic acid targets or the analysis of oncology markers or the like.

The most prominent and widely used method for amplification (and detection/quantitation) of nucleic acid targets is the Polymerase Chain Reaction (PCR). Other amplification techniques include Ligase Chain Reaction, Polymerase Ligase Chain Reaction, Gap-LCR, Repair Chain Reaction, 3 SR, NASBA, Strand Displacement Amplification (SDA), Transcription Mediated Amplification (TMA), and Qβ-amplification.

Automated systems for PCR-based analysis often make use of a real-time detection of product amplification during the PCR process in the same reaction vessel. Key to such methods is the use of modified oligonucleotides carrying reporter groups or labels. PCR utilizes a polymerase enzyme (U.S. Pat. Nos. 4,683,195 and 4,683,202). Related significant improvements are, e.g., real-time detection of amplified products during PCR utilizing modified oligonucleotides carrying reporter groups or labels known as hydrolization or 5'-nuclease probes such as used in commercial assays on COBAS® TaqMan® (U.S. Pat. Nos. 5,210,015 and 5,487,972). Other improved amplification and detection methods are known as Molecular Beacons technology (International Patent Publication No. WO 95/13399) or methods utilizing an oligonucleotide comprising a minor groove binder (MGB) portion (International Patent Publication Nos. WO 03/062445 and WO 2006/135765). It is further known that the use of primers containing an added oligonucleotide with a high GC content at the 5' terminus of at least one of these primers displays an improvement in amplification efficiency (Liu, et al., Genome Research 7:389-398 (1997); International Patent Publication No. WO 01/94638; and U.S. Patent Publication No. US 2004/0110182). The final quantity of the amplified product after approximately 12 to 40 cycles of PCR is markedly higher for primers to which, e.g., a GGAC unit has been added to the 5' termini than for the unmodified primers.

Afonina, et al., BioTechniques 43(3):1-3 (2007); International Patent Publication No. WO 2006/135765 describe the increase of real-time PCR fluorescent signal and thereby obtaining improved amplification efficiency by using primers with short adenine and thymine rich flaps, scattered randomly, at the 5' terminus and minor groove binder (MGB) fluorescent hybridization probes.

Similarly, Babiel, et al. (U.S. Pat. No. 9,447,476) describe how the addition of polyN to primers can result in the reduction or suppression of the formation of unwanted high molecular weight products, thereby avoiding false-negative or false-positive results.

Thus, there is always a need in the art for improvements on existing methods. For example, there is a need in the art to provide a method for simple and reliable detection and quantitation of a nucleic acid target. There is, in particular a need for improving the efficiency of DNA amplification and detection/quantitation.

SUMMARY OF THE INVENTION

Certain embodiments in the present disclosure relate to new methods and uses for amplification, detection, and quantitation of target nucleic acid in a sample (e.g., a biological or non-biological sample). For example, certain embodiments of the present disclosure relate to singleplex or multiplex detection and quantitating of a microbe, such as virus (e.g., HPV, WNV, HAV, HBV, HCV, and HIV) by a real-time polymerase chain reaction (PCR) in a single test tube or reaction vessel. The improvement is based on the use of a non-extending helper oligonucleotide in an amplification reaction, such as PCR. It is believed that the non-extending helper oligonucleotide acts as a sort of a helper oligonucleotide or a helper primer, in that it facilitates and enhances amplification that is mediated by the (extending) primers. It is further believed that the presence of the non-extending helper oligonucleotide reduces or lowers the Gibbs Free Energy of the secondary structure of the target region of the target nucleic acid. In some cases, the non-extending helper oligonucleotide is believed to reduce/lower the Gibbs Free energy of the secondary structure of the primer-binding region of the target nucleic acid. The non-extending helper oligonucleotide may anneal within the same region as one or more of the primers. However, the non-extending helper oligonucleotide does not extend, in contrast to the one or more primers. That is, the non-extending helper oligonucleotide does not extend to generate an amplicon. Instead of extending, the non-extending helper oligonucleotide facilitates and increases the target accessibility of the primer or primers, which do extend and generate amplicons. That is, like the extending primer, the non-extending helper oligonucleotide anneals to the target nucleic acid, but unlike the extending primer, the non-extending helper oligonucleotide does not extend. There are many ways to prevent an oligonucleotide from extending, which are and would be well known by one of ordinary skill in the art. For example, the addition of poly(A) sequences to the 3'-end of the oligonucleotide prevents extension. It is further believed that the poly(A) sequences do not likely anneal to any portion of the target nucleic acid, which thereby destabilizes the interaction between the non-extending helper oligonucleotide and the target nucleic acid, which in turn, opens up the secondary structure and allowing for displacement of the non-extending helper oligonucleotide with the (extending) primer. Additionally, replacing the 3'-OH group with a phosphate group (i.e., phosphorylation) also prevents extension. It is believed that the non-extending helper oligonucleotide assists the amplification by reducing the Gibbs Free Energy of the secondary structure in the primer binding region of the target nucleic acid, thereby improving the accessibility of one or more of the primers that extend (see, FIGS. 2 and 4). This results in an improvement in PCR amplification, such that more PCR product (i.e., amplicon) accumulates in the presence of the non-extending helper oligonucleotide than in the absence of the non-extending helper oligonucleotide (see, FIGS. 1 and 3). That is, the overall efficiency of the PCR assay is improved and/or enhanced by the non-extending helper oligonucleotide. Because the efficiency of the PCR assay is improved, it is possible to successfully amplify even small amounts of starting material (i.e., low copy numbers), in the presence of the non-extending helper oligonucleotide. Thus, the non-extending helper oligonucleotide also increases the sensitivity of the assay.

Embodiments include methods of detection and quantitation of a target nucleic acid comprising performing at least one cycling step, which may include an amplifying step and a hybridizing step. Furthermore, embodiments include primers, probes, and one or more non-extending helper oligonucleotides, and kits that are designed for the detection and quantitation of a target nucleic acid in a single reaction vessel or tube.

The present disclosure also provides for methods of detecting the presence or absence of a target nucleic acid in a biological sample from an individual. These methods can be employed to detect the presence or absence of a target nucleic acid in plasma, for use in blood screening and diagnostic testing. Additionally, the same test may be used by someone experienced in the art to assess urine and other sample types to detect and/or quantitate a target nucleic acid. Such methods generally include performing at least one cycling step, which includes an amplifying step and a dye-binding step. Typically, the amplifying step includes contacting the sample with a plurality of pairs of oligonucleotide primers and, in this case, one or more non-extending helper oligonucleotides, to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of a target nucleic acid in the sample, and wherein the absence of binding is indicative of the absence of target nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of a nucleic acid nucleic acid.

In a further embodiment, a kit for detecting and/or quantitating one or more target nucleic acids is provided. The kit can include one or more sets of primers specific for amplification of the target nucleic acid; one or more non-extending helper oligonucleotide; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, non-extending helper oligonucleotides, probes, and fluorophoric moieties to detect the presence or absence of amplification products/target nucleic acids in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
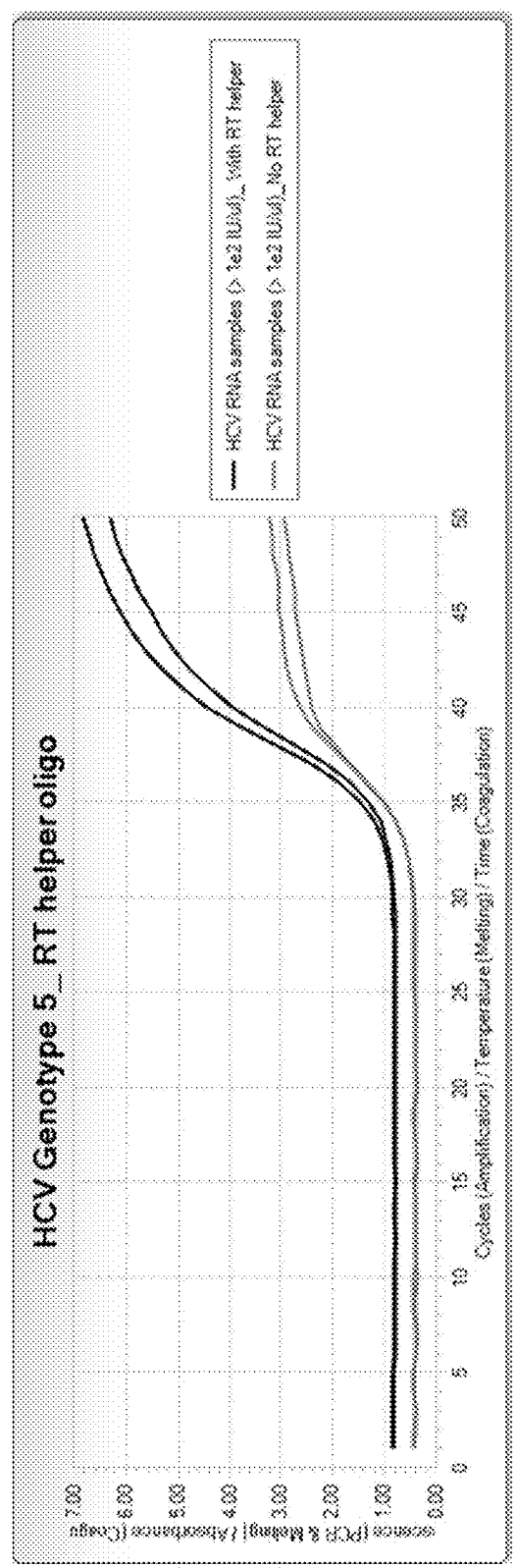
FIG. 1 shows real-time PCR growth curves of an experiment showing the primers, probes, and non-extending helper oligonucleotides and probes specific for a target nucleic acid (of HCV).

The present invention relates to new and improved methods and uses for amplifying, detecting, and quantitating a nucleic acid target that may be present in a sample (e.g., a biological sample) comprising at least a primer pair for generating an amplicon, a detectable probe specific for the amplicon, and a non-extending helper oligonucleotide. The improvement is, in particular, based on the fact that the amplification (i.e., generation of the amplicon) is enhanced and increased in the presence of a non-extending helper oligonucleotide. That is, the non-extending helper oligonucleotide enhances and improves the activity and efficiency of one or more of the primers that extends, thereby improving and increasing the efficiency of the PCR reaction. This has the effect of increasing the sensitivity of the assay. This present invention can be used for any number of applications, including, but not limited to the amplification, and detection/quantitation of microbial nucleic acids (e.g., viral or bacterial nucleic acid). Examples of viruses for use with the present invention include HPV, WNV, HAV, HBV, HCV, and HIV.

Diagnosis of a microbial (e.g., viral or bacterial) infection by nucleic acid amplification provides a method for rapidly, accurately, reliably, specifically, and sensitively detecting and/or quantitating the infection. A real-time reverse-transcriptase PCR assay for detecting and/or quantitating microbial nucleic acids in a non-biological or biological sample is described herein. Primers and probes for detecting and/or quantitating target nucleic acid (such as microbial nucleic acid, like viral or bacterial nucleic acid) are provided, as are articles of manufacture or kits containing such primers and probes. The increased specificity and sensitivity of real-time PCR for detection of target nucleic acid compared to other methods, as well as the improved features of real-time PCR including sample containment and real-time detection and quantitating of the amplified product, make feasible the implementation of this technology for routine diagnosis of microbial infections (e.g., viral or bacterial infections) in the clinical laboratory. Additionally, this technology may be employed for blood screening as well as for prognosis. Such a detection assay may also be multiplexed with other assays for the detection of other target nucleic acids (e.g., other microbial nucleic acids, or other/different genotypes of the same microbe), in parallel.

The present disclosure includes, by way of example, oligonucleotide primers, non-extending helper oligonucleotides, and fluorescent labeled hydrolysis probes that hybridize to the HCV genome, in order to specifically identify HCV using, e.g., TaqMan® detection technology.

The term "primer(s)" or "extending primer(s)" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released.

Specifically, the disclosed methods may include performing at least one cycling step that includes amplifying one or more portions of the nucleic acid molecule gene target from a sample using one or more pairs of primers. "Primer(s)" or "extending primer(s)" as used herein refer to oligonucleotide primers that specifically anneal to nucleic acid sequences found in the target region in the sample, and initiate DNA synthesis therefrom under appropriate conditions producing the respective amplification products. The amplification product should contain the nucleic acid sequences that are complementary to one or more detectable probes specific for the target nucleic acid. "Probe(s)" or "detectable probe(s)" as used herein refer to oligonucleotide probes that specifically anneal to nucleic acid sequences found in target region in the sample. Each cycling step includes an amplification step, a hybridization step, and a detection step, in which the sample is contacted with the one or more detectable probes for detection of the presence or absence of target nucleic acid in the target region of the sample.

As used herein, the term "amplifying" refers to the process of synthesizing nucleic acid molecules that are complementary to one or both strands of a template nucleic acid molecule (e.g., nucleic acid molecules from a microbe, such as virus or bacteria). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus.* Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a phosphate, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl ribo-U, 2'-0-methyl ribo-C, an N4-ethyl-dC, an N6-methyl-dA, a 5-propynyl dU, a 5-propynyl dC, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection of Target Nucleic Acid

The present disclosure provides methods to detect and quantitate a target nucleic acid in a sample by amplifying a portion of the target nucleic acid sequence. By way of example, provided are methods to detect and quantitate HCV in a sample by amplifying a portion of the HCV nucleic acid sequence. Specifically, primers, non-extending helper oligonucleotides, and probes to amplify and detect/quantitate HCV nucleic acid molecule targets are provided by the embodiments in the present disclosure.

For amplification, detection, and quantitation of HCV, primers, non-extending helper oligonucleotides, and probes are provided. HCV nucleic acids other than those exemplified herein can also be used to detect HCV in a sample. For example, functional variants can be evaluated for specificity and/or sensitivity by those of skill in the art using routine methods. Representative functional variants can include, e.g., one or more deletions, insertions, and/or substitutions in the HCV nucleic acids disclosed herein.

More specifically, embodiments of the oligonucleotides each include a nucleic acid with a sequence selected from SEQ ID NOs:1-5, a substantially identical variant thereof in which the variant has at least, e.g., 80%, 90%, or 95% sequence identity to one of SEQ ID NOs:1-5, or a complement of SEQ ID NOs:1-5 and the variant. The forward primer, reverse primers, and detectable probes (SEQ ID NOs:1-4) are from a commercially available HCV genotyping assay (Cobas® HCV GT for use with the Cobas® 4800 system, Roche).

TABLE 1

HCV Oligonucleotides

| Oligo Type | Oligo Name | SEQ ID NO: | Sequence | Modifications |
|---|---|---|---|---|
| Forward Primer | AYHCV5001TBB | 1 | TGGGCAGGGTGGTTGCTK | K: t-Butyl Benzyl-dC |
| Reverse Primer | AYHCV5002TBB | 2 | GTTGCATAGTTTACCCCGTCCTCAJ | J: t-Butyl Benzyl-dA |
| Reverse Primer | AYHCV5012BB | 3 | GTTGCATAGTTTATCCCGTCCTCAJ | J: t-Butyl Benzyl-dA |
| Detectable Probe | AYHCV5012HBH6 | 4 | EATCCCGQCTCGTAGGCGGCCCCGTTGP | Q: BHQ-2<br>P: Phosphate<br>E: Threo-HEX |
| Non-Extending Helper Oligo | RM_111 | 5 | GTTGCATAGTTTATCCCGTCTTCAAGAACCTTCACACCGTGTGCGAAAAAAAA | |

In one embodiment, the above described sets of HCV primers, non-extending helper oligonucleotides, and probes are used in order to provide for detection of HCV in a biological sample suspected of containing HCV (Table 1). The sets of primers, non-extending helper oligonucleotides, and probes may comprise or consist of the primers, non-extending helper oligonucleotide, and probes specific for the HCV nucleic acid sequences, comprising or consisting of the nucleic acid sequences of SEQ ID NOs:1-5. In another embodiment, the primers, non-extending helper oligonucleotides, and probes for the HCV target comprise or consist of a functionally active variant of any of the primers, non-extending helper oligonucleotides, and probes of SEQ ID NOs:1-5.

A functionally active variant of any of the primers, non-extending helper oligonucleotides, and/or probes of SEQ ID NOs:1-5 may be identified by using the primers, non-extending helper oligonucleotides, and/or probes in the disclosed methods. A functionally active variant of a primer, non-extending helper oligonucleotides, and/or probe of any of the SEQ ID NOs:1-5 pertains to a primer, non-extending helper oligonucleotides, and/or probe which provide a similar or higher specificity and sensitivity in the described method or kit as compared to the respective sequence of SEQ ID NOs:1-5.

The variant may, e.g., vary from the sequence of SEQ ID NOs:1-5 by one or more nucleotide additions, deletions or substitutions such as one or more nucleotide additions, deletions or substitutions at the 5' end and/or the 3' end of the respective sequence of SEQ ID NOs:1-5. As detailed above, a primer, non-extending helper oligonucleotide, and/or probe may be chemically modified, i.e., a primer, non-extending helper oligonucleotide, and/or probe may comprise a modified nucleotide or a non-nucleotide compound. A primer, non-extending helper oligonucleotide, and/or probe is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule corresponding to a target region. Oligonucleotides corresponding to, e.g., alternative portions of the target can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

Oligonucleotides of the present invention include "helper oligonucleotide(s)" or "non-extending helper oligonucleotide(s)." In some cases, the non-extending helper oligonucleotide will anneal, in part, to a portion within the target nucleic acid. Because the non-extending helper oligonucleotides is believed to facilitate access of the extending primer or primers to the target nucleic acid, the non-extending helper oligonucleotide may act on or near the same location as where the extending primer will anneal. Therefore, in some instances, the non-extending helper oligonucleotide will anneal, in part or in whole, to the same region within the target nucleic acid as the extending primer. That is, in some cases, the non-extending helper oligonucleotide and the extending primer will anneal to the same portion, in part or in whole, within the target nucleic acid. Thus, in some cases, the non-extending helper oligonucleotide and the extending primer may share the same sequences, in part or in whole. It is believed that the non-extending helper oligonucleotide lowers the Gibbs free energy of the secondary structure of the target nucleic acid. This then facilitates annealing of one or more extending primers to the target, which would then initiate extension via DNA polymerases (i.e., nucleic acid synthesis). Thus, the non-extending helper oligonucleotide In order to prevent the helper oligonucleotide itself from extending, any number of modifications may be made to the helper oligonucleotide. Such modifications would be well known to one of ordinary skill in the art. Examples of such modifications include the addition of poly(A) nucleotides to the 3'-terminus of the helper oligonucleotide, and/or by replacing the 3'-OH group with a phosphate group (i.e., phosphorylation). It is believed that the addition of poly(A) sequences (which will not likely anneal to the target nucleic acid) destabilizes the interaction between the non-extending helper oligonucleotide and the target nucleic acid, thereby opening up the secondary structure, which facilitates access of the target nucleic acid region to the (extending) primer.

In addition to a set of primers, the methods may use one or more probes in order to detect the presence or absence of a target nucleic acid. The term "probe" refers to synthetically or biologically produced nucleic acids (DNA or RNA), which by design or selection, contain specific nucleotide sequences that allow them to hybridize, under defined predetermined stringencies specifically (i.e., preferentially), to "target nucleic acids." A "probe" can be referred to as a "detection probe" meaning that it detects the target nucleic acid.

In some embodiments, the probes can be labeled with at least one fluorescent label. In one embodiment, the probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NO:4.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one primers, non-extending helper oligonucleotides, and probes nucleic acid molecules. For example, constructs can include vectors each containing one of microbial target primers, non-extending helper oligonucleotides, and probes nucleic acid molecules (e.g., SEQ ID NOs:1, 2, 3, 4, and 5, for HCV). Constructs can be used, for example, as control template nucleic acid molecules. Vectors suitable for use are commercially available and/or produced by recombinant nucleic acid technology methods routine in the art. Nucleic acid molecules can be obtained, for example, by chemical synthesis, direct cloning from target region, or by nucleic acid amplification.

Constructs suitable for use in the methods typically include sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing the target nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). These two oligonucleotide primers are typically a forward primer and a reverse primer. Primers useful in some embodiments include oligonucleotides capable of acting as points of initiation of nucleic acid synthesis within the described HCV nucleic acid sequences (e.g., SEQ ID NOs:1, 2, and 3). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus (e.g., HCV as well as other flaviviruses), is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ target nucleic acid such as RNA or DNA (cDNA). The template nucleic acid need not be purified; it may be a minor fraction of a complex mixture, such as microbial target nucleic acid contained in human cells. Microbial nucleic acid molecules, such as from viruses, such as HPV, WNV, HAV, HBV, HCV, and HIV, may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs:1-3 for HCV) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety (e.g., FAM) and a corresponding quencher (e.g., BlackHole Quenchers™ (BHQ) (such as BHQ2)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ) (such as BHQ2), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodaminexisothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in International Patent Publication No. WO 84/03285. International Patent Publication No. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of Amplified Target Nucleic Acid Product (Amplicon)

The present disclosure provides methods for detecting and quantitating target nucleic (including microbial target nucleic acids, such as HPV, WNV, HAV, HBV, HCV, and HIV) in a biological or non-biological sample. Methods provided avoid problems of sample contamination, false negatives, and false positives. The methods include performing at least one cycling step that includes amplifying a portion of target nucleic acid molecules from a sample (e.g., HPV, WNV, HAV, HBV, HCV, or HIV) using one or more pairs of target primers, a non-extending helper oligonucleotide, and a FRET detecting step. Multiple cycling steps are performed, preferably in a thermocycler. Methods can be performed using the target primers, non-extending helper oligonucleotides, and probes to detect the presence of a target nucleic acid (e.g., HPV, WNV, HAV, HBV, HCV, or HIV). Detection of the target nucleic acid (by, e.g., a probe) indicates the presence of the target nucleic acid (e.g., HPV, WNV, HAV, HBV, HCV, or HIV) in the sample.

As described herein, amplification products can be detected using labeled hybridization probes that take advantage of FRET technology. One FRET format utilizes TaqMan® technology to detect the presence or absence of an amplification product, and hence, the presence or absence of HCV virus. TaqMan® technology utilizes one single-stranded hybridization probe labeled with, e.g., one fluorescent dye (e.g., HEX) and one quencher (e.g., BHQ or BHQ-2), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of a target nucleic acid/amplification product in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of HCV genomes). If amplification of target nucleic acid occurs and an amplification product is produced, the step of hybridizing results in a detectable signal based upon FRET between the members of the pair of probes.

Generally, the presence of FRET indicates the presence of the target nucleic acid in the sample, and the absence of FRET indicates the absence of the target nucleic acid in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to respiratory specimens, urine, fecal specimens, blood specimens, plasma, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release the target nucleic acid (microbial target nucleic acids, such as HPV, WNV, HAV, HBV, HCV, and HIV) or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the target nucleic acid probes from the target nucleic acid amplification products can confirm the presence or absence of target nucleic acid in the sample (e.g., microbial target nucleic acids, such as HPV, WNV, HAV, HBV, HCV, and HIV).

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: International Patent Publication Nos. WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3 SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect and quantitate a target nucleic acid (e.g., microbial target nucleic acids, such as HPV, WNV, HAV, HBV, HCV, and HIV). An article of manufacture can include primers, non-extending helper oligonucleotides, and probes used to detect the gene target (e.g., microbial target nucleic acids, such as HPV, WNV, HAV, HBV, HCV, and HIV), together with suitable packaging materials. Representative primers and probes for detection and quantitation of a target nucleic acid (e.g., microbial target nucleic acids, such as HPV, WNV, HAV, HBV, HCV, and HIV) are capable of hybridizing to target nucleic acid molecules. Representative non-extending helper oligonucleotides are capable of annealing/hybridizing, in part or in whole, to the target nucleic acid molecules. In some cases, the non-extending helper oligonucleotide and the (extending) primers anneal/hybridize to the same portion, in part or in whole, of the target nucleic acid. That is, the non-extending helper oligonucleotide may be designed in the primer-binding region. Alternatively, the non-extending helper oligonucleotide and the (extending) primers do not anneal/hybridize to the same portion of the target nucleic acid. In addition, the kits may also include suitably packaged reagents and materials needed for DNA immobilization, hybridization, detection, quantitation, such as solid supports, buffers, enzymes, and DNA standards. Methods of designing primers, non-extending helper oligonucleotides, and probes are disclosed herein, and representative examples of primers, non-extending helper oligonucleotides, and probes that amplify and hybridize to target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the target nucleic acid probes (e.g., probes specific for microbial target nucleic acids, such as HPV, WNV, HAV, HBV, HCV, and HIV). Examples of suitable FRET donor fluorescent moieties and corresponding acceptor fluorescent moieties are provided above.

Articles of manufacture can also contain a package insert or package label having instructions thereon for using the primers, non-extending helper oligonucleotides, and probes to detect and quantitate target nucleic acid (e.g., microbial target nucleic acids, such as HPV, WNV, HAV, HBV, HCV, and HIV) in a sample. Articles of manufacture may additionally include reagents for carrying out the methods disclosed herein (e.g., buffers, polymerase enzymes (e.g., DNA polymerase), nucleoside triphosphate monomers or other nucleoside monomers, co-factors, or agents to prevent contamination). Such reagents may be specific for one of the commercially available instruments described herein.

Embodiments of the present disclosure also provide for a set of primers, one or more non-extending helper oligonucleotides, and one or more detectable probes for the detection of a target nucleic acid (e.g., microbial target nucleic acids, such as HPV, WNV, HAV, HBV, HCV, and HIV) in a sample.

Reaction Mixtures

Embodiments of the present disclosure further provide for reaction mixtures to amplify, detect, and quantitate a target nucleic acid (e.g., microbial target nucleic acids, such as HPV, WNV, HAV, HBV, HCV, and HIV). A reaction mixture can include primers, non-extending helper oligonucleotides, and probes used to detect the gene target (e.g., microbial target nucleic acids, such as HPV, WNV, HAV, HBV, HCV, and HIV), together with suitable packaging materials. Representative primers, non-extending helper oligonucleotides, and probes for detection and quantitation of a target nucleic acid (e.g., microbial target nucleic acids, such as HPV, WNV, HAV, HBV, HCV, and HIV) are capable of hybridizing to target nucleic acid molecules. In addition, the kits may also include suitably packaged reagents and materials needed for DNA immobilization, hybridization, detection, quantitation, such as solid supports, buffers, enzymes, and DNA standards. Methods of designing primers, non-extending helper oligonucleotides, and probes are disclosed herein, and representative examples of primers, non-extending helper oligonucleotides, and probes that amplify and hybridize to target nucleic acid molecules are provided.

Reaction mixtures can also include one or more fluorescent moieties for labeling the probes or, alternatively, the probes supplied with the kit can be labeled. For example, a reaction mixture may include a donor and/or an acceptor fluorescent moiety for labeling the target nucleic acid probes (e.g., probes specific for microbial target nucleic acids, such as HPV, WNV, HAV, HBV, HCV, and HIV). Examples of suitable FRET donor fluorescent moieties and corresponding acceptor fluorescent moieties are provided above.

Reaction mixtures may additionally include reagents for carrying out the methods disclosed herein (e.g., buffers, polymerase enzymes (e.g., DNA polymerase), nucleoside triphosphate monomers or other nucleoside monomers, co-factors, or agents to prevent contamination). Such reagents may be specific for one of the commercially available instruments described herein.

Embodiments of the present disclosure also provide for a set of primers, one or more non-extending helper oligonucleotides, and one or more detectable probes for the detection of a target nucleic acid (e.g., microbial target nucleic acids, such as HPV, WNV, HAV, HBV, HCV, and HIV) in a sample.

One embodiment of the invention is directed to a method for detecting and/or quantitating a target nucleic acid in a sample comprising: (a) contacting nucleic acids in the sample with amplification reagents, the amplification reagents comprising: at least an enzyme comprising DNA polymerase activity; at least nucleoside triphosphate monomers or other nucleoside monomers; at least one forward primer specific for the target nucleic acid, or at least one reverse primer specific for the target nucleic acid, or a combination thereof, for generating at least one amplicon; at least one non-extending helper oligonucleotide, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and at least one detectable probe specific for the amplicon or at least one DNA binding dye; (b) incubating the nucleic acids with the amplification reagents for a period of time and under conditions sufficient for an amplification reaction to occur; and (c) detecting the amplicon with the at least one detectable probe or the at least one DNA binding dye. In another embodiment, the target nucleic acid is a microbial nucleic acid (such as a viral nucleic acid and/or a bacterial nucleic acid). In some embodiments, the viral nucleic acid is a nucleic acid of Human Papilloma Virus (HPV), West Nile Virus (WNV), Human Immunodeficiency Virus (HIV), Hepatitis A Virus (HAV), Hepatitis B Virus (HBV), or Hepatitis C Virus (HCV). In a related embodiment, the viral nucleic acid is a nucleic acid of Hepatitis C Virus (HCV), including, e.g., HCV Genotype 5. In another embodiment the at least one non-extending helper oligonucleotide comprises a poly(A) sequence at the 3'-end of the at least one non-extending helper oligonucleotide. In a related embodiment, the poly(A) sequence is between 4-12 nucleotides in length, such as about 8 nucleotides in length. In another embodiment, the at least one non-extending helper oligonucleotide comprises the sequence of SEQ ID NO:5, or a complementary sequence thereof. In another embodiment, the at least one forward primer comprises the sequence of SEQ ID NO:1, or a complementary sequence thereof. In another embodiment, the at least one reverse primer comprises the sequence selected from the group consisting of SEQ ID NOs:2 and 3, or a complementary sequence thereof. In another embodiment, the at least one probe comprises the sequence of SEQ ID NO:4, or a complementary sequence thereof. In yet another embodiment, the at least one forward primer comprises the sequence of SEQ ID NO:1, or a complementary sequence thereof; the at least one reverse primer comprises the sequence selected from the group consisting of SEQ ID NOs:2 and 3, or a complementary sequence thereof and the at least one probe comprises the sequence of SEQ ID NO:4, or a complementary sequence thereof.

Another embodiment of the present invention is directed to a method for detecting and/or quantitating an HCV nucleic acid in a sample comprising: (a) contacting nucleic acids in the sample with amplification reagents, the amplification reagents comprising: at least an enzyme comprising DNA polymerase activity; at least nucleoside triphosphate monomers or other nucleoside monomers; at least one forward primer specific for the target nucleic acid, or at least one reverse primer specific for the target nucleic acid, or a combination thereof, for generating at least one amplicon; at least one non-extending helper oligonucleotide, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and at least one detectable probe specific for the amplicon or at least one DNA binding dye; (b) incubating the nucleic acids with the amplification reagents for a period of time and under conditions sufficient for an amplification reaction to occur; and (c) detecting the amplicon with the at least one detectable probe or the at least one DNA binding dye. In another embodiment, the at least one non-extending helper oligonucleotide comprises a poly(A) sequence at the 3'-end of the at least one non-extending helper oligonucleotide. In another embodiment, the poly(A) sequence is between 4-12 nucleotides in length, for example, about 8 nucleotides in length. In another embodiment, the HCV is HCV Genotype 5. In another embodiment, the at least one non-extending helper oligonucleotide comprises the sequence of SEQ ID NO:5, or a complementary sequence thereof. In a related embodiment, the at least one forward primer comprises the sequence of SEQ ID NO:1, or a complementary sequence thereof. In another embodiment, the at least one reverse primer comprises the sequence selected from the group consisting of SEQ ID NOs:2 and 3, or a complementary sequence thereof. In another embodiment, the at least one probe comprises the sequence of SEQ ID NO:4, or a complementary sequence thereof. In another embodiment, the at least one forward primer comprises the sequence of SEQ ID NO:1, or a complementary sequence thereof; the at least one reverse primer comprises the sequence selected from the group consisting of SEQ ID NOs:2 and/or 3, or a complementary sequence thereof; and the at least one probe comprises the sequence of SEQ ID NO:4, or a complementary sequence thereof.

Another embodiment of the present invention is directed to a kit for amplifying and detecting and/or quantitating a target nucleic acid in a sample comprising amplification reagents, the amplification reagents comprising: (a) an enzyme comprising DNA polymerase activity; (b) nucleoside triphosphate monomers or other nucleoside monomers; (c) at least one forward primer or at least one reverse primer specific for the target nucleic acid, or a combination thereof; (d) at least one non-extending helper oligonucleotide, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and (e) at least one detectable probe for the target nucleic acid or a DNA binding dye. In another embodiment, the target nucleic acid is a microbial nucleic acid (such as a viral nucleic acid or a bacterial nucleic acid). In a related embodiment, the viral nucleic acid is a nucleic acid of HPV, WNV, HIV, HAV, HBV, or HCV. In a more particular embodiment, the viral nucleic acid is a nucleic acid of HCV, including, for example, HCV Genotype 5. In another embodiment, the at least one non-extending helper oligonucleotide comprises a poly(A) sequence at the 3'-end of the at least one non-extending helper oligonucleotide. In another embodiment, the poly(A) sequence is between 4-12 nucleotides in length, for example, about 8 nucleotides in length. In another embodiment, the at least one non-extending helper oligonucleotide comprises the sequence of SEQ ID NO:5, or a complementary sequence thereof. In another embodiment, the at least one forward primer comprises the sequence of SEQ ID NO:1, or a complementary sequence thereof. In another embodiment, the at least one reverse primer comprises the sequence selected from the group consisting of SEQ ID NOs:2 and 3, or a complementary sequence thereof. In another embodiment, the at least one probe comprises the sequence of SEQ ID NO:4, or a complementary sequence thereof. In another embodiment, the at least one forward primer comprises the sequence of SEQ ID NO:1, or a complementary sequence thereof; the at least one reverse primer comprises the sequence selected from the group consisting of SEQ ID NOs:2 and 3, or a complementary sequence thereof; and the at least one probe comprises the sequence of SEQ ID NO:4, or a complementary sequence thereof.

A related embodiment of the present invention is directed to a kit for amplifying and detecting and/or quantitating a HCV nucleic acid in a sample comprising amplification reagents, the amplification reagents comprising: (a) an enzyme comprising DNA polymerase activity; (b) nucleoside triphosphate monomers or other nucleoside monomers; (c) at least one forward primer or at least one reverse primer specific for the target nucleic acid, or a combination thereof; (d) at least one non-extending helper oligonucleotide, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and (e) at least one detectable probe for the target nucleic acid or a DNA binding dye. In another embodiment, the at least one non-extending helper oligonucleotide comprises a poly(A) sequence at the 3'-end of the at least one non-extending helper oligonucleotide. In another embodiment, the poly(A) sequence is between 4-12 nucleotides in length, for example, about 8 nucleotides in length. In another embodiment, the HCV is HCV Genotype 5. In another embodiment, the at least one non-extending helper oligonucleotide comprises the sequence of SEQ ID NO:5, or a complementary sequence thereof. In a related embodiment, the at least one forward primer comprises the sequence of SEQ ID NO:1, or a complementary sequence thereof. In another embodiment, the at least one reverse primer comprises the sequence selected from the group consisting of SEQ ID NOs:2 and 3, or a complementary sequences thereof. In another embodiment, the at least one probe comprises the sequence of SEQ ID NO:4, or a complementary sequence thereof. In another embodiment, the at least one forward primer comprises the sequence of SEQ ID NO:1, or a complementary sequence thereof the at least one reverse primer comprises the sequence selected from the group consisting of SEQ ID NOs:2 and 3, or a complementary sequence thereof and the at least one probe comprises the sequence of SEQ ID NO:4, or a complementary sequence thereof.

Yet another embodiment of the present invention is directed to a reaction mixture effective to amplify and detect and/or quantitate a target nucleic acid in a sample comprising amplification reagents comprising: (a) a sample; (b) an enzyme comprising DNA polymerase activity; (c) nucleoside triphosphate monomers or other nucleoside monomers; (d) at least one forward primer or at least one reverse primer specific for the target nucleic acid, or a combination thereof (e) at least one non-extending helper oligonucleotide, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and (f) at least one detectable probe for the target nucleic acid or a DNA binding dye. In another embodiment, the target nucleic acid is a microbial nucleic acid. In another embodiment, the microbial nucleic acid is a viral nucleic acid. In another embodiment, the microbial nucleic acid is a bacterial nucleic acid. In another embodiment, the viral nucleic acid is a nucleic acid of HPV, WNV, HIV, HAV, HBV, or HCV. In a particular embodiment, the viral nucleic acid is a nucleic acid of HCV, including, for example, HCV Genotype 5. In another embodiment, the at least one non-extending helper oligonucleotide comprises a poly(A) sequence at the 3'-end of the at least one non-extending helper oligonucleotide. In another embodiment, the poly(A) sequence is between 4-12 nucleotides in length, for example, about 8 nucleotides in length. In another embodiment, the at least one non-extending helper oligonucleotide comprises the sequence of SEQ ID NO:5, or a complementary sequence thereof. In another embodiment, the at least one forward primer comprises the sequence of SEQ ID NO:1, or a complementary sequence thereof. In another embodiment, the at least one reverse primer comprises the sequence selected from the group consisting of SEQ ID NOs:2 and 3, or a complementary sequence thereof. In another embodiment, the at least one probe comprises the sequence of SEQ ID NO:4, or a complementary sequence thereof. In another embodiment, the at least one forward primer comprises the sequence of SEQ ID NO:1, or a complementary sequence thereof the at least one reverse primer comprises the sequence selected from the group consisting of SEQ ID NOs:2 and 3, or a complementary sequence thereof; and the at least one probe comprises the sequence of SEQ ID NO:4, or a complementary sequence thereof.

A related embodiment of the present invention is directed to a reaction mixture effective to amplify and detect and/or quantitate a HCV nucleic acid in a sample, comprising amplification reagents comprising: (a) a sample; (b) an enzyme comprising DNA polymerase activity; (c) nucleoside triphosphate monomers or other nucleoside monomers; (d) at least one forward primer or at least one reverse primer specific for the target nucleic acid, or a combination thereof; (e) at least one non-extending helper oligonucleotide, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and (f) at least one detectable probe for the target nucleic acid or a DNA binding dye. In another embodiment, the at least one non-extending helper oligonucleotide comprises a poly(A) sequence at the 3'-end of the at least one non-extending helper oligonucleotide. In another embodiment, the poly(A) sequence is between 4-12 nucleotides in length, for example about 8 nucleotides in length. In one embodiment, the HCV is HCV Genotype 5. In another embodiment, the at least one non-extending helper oligonucleotide comprises the sequence of SEQ ID NO:5, or a complementary sequence thereof. In another embodiment, the at least one forward primer comprises the sequence of SEQ ID NO:1, or a complementary sequence thereof. In another embodiment, the at least one reverse primer comprises the sequence selected from the group consisting of SEQ ID NOs:2 and 3, or a complementary sequences thereof. In another embodiment, the at least one probe comprises the sequence of SEQ ID NO:4, or a complementary sequence thereof. In another embodiment, the at least one forward primer comprises the sequence of SEQ ID NO:1, or a complementary sequence thereof the at least one reverse primer comprises the sequence selected from the group consisting of SEQ ID NOs:2 and 3, or a complementary sequence thereof and the at least one probe comprises the sequence of SEQ ID NO:4, or a complementary sequence thereof.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

Example 1: Detection of HCV by Real-Time PCR

RNA samples used for a real-time PCR assay were extracted from a HCV-positive human plasma sample. Reagents used include Cobas® 6800/8800 generic PCR Master Mix, with the profile and conditions for use with the Cobas® 6800/8800, and using TaqMan® detection and quantitation technology. In 50 µl of PCR reaction, the final concentrations were as follows: forward and reverse primers ranged from 0.2-0.5 µM; non-extending helper oligonucleotide was at 0.20 µM; and probe was at 0.12 µM. It is believed that the forward primer, reverse primers, and non-extending helper oligonucleotides at a concentration within a range of 0.10 µM-0.50 µM would be effective.

To demonstrate the effect of the non-extending helper oligonucleotide, a real-time PCR assay using HCV-positive human plasma samples was conducted in duplicate with the following two experimental conditions: (1) real-time PCR with primer pairs and probe only (i.e., without non-extending helper oligonucleotide); and (2) real-time PCR with primer pairs, non-extending helper oligonucleotide, and probe. The oligonucleotides specific for HCV Genotype 5 used for the real-time PCR assay were SEQ ID NO:1 for the forward primer, SEQ ID NOs:2 and 3 for the reverse primers, SEQ ID NO:5 for the non-extending helper oligonucleotide, and SEQ ID NO:4 for the probe. The non-extending helper oligonucleotide (SEQ ID NO:5) is a 53 base pair unlabeled oligonucleotide with a poly(A) tail at its 3'-end and is designed in the reverse primer binding core region of the HCV genome.

Figure 2:
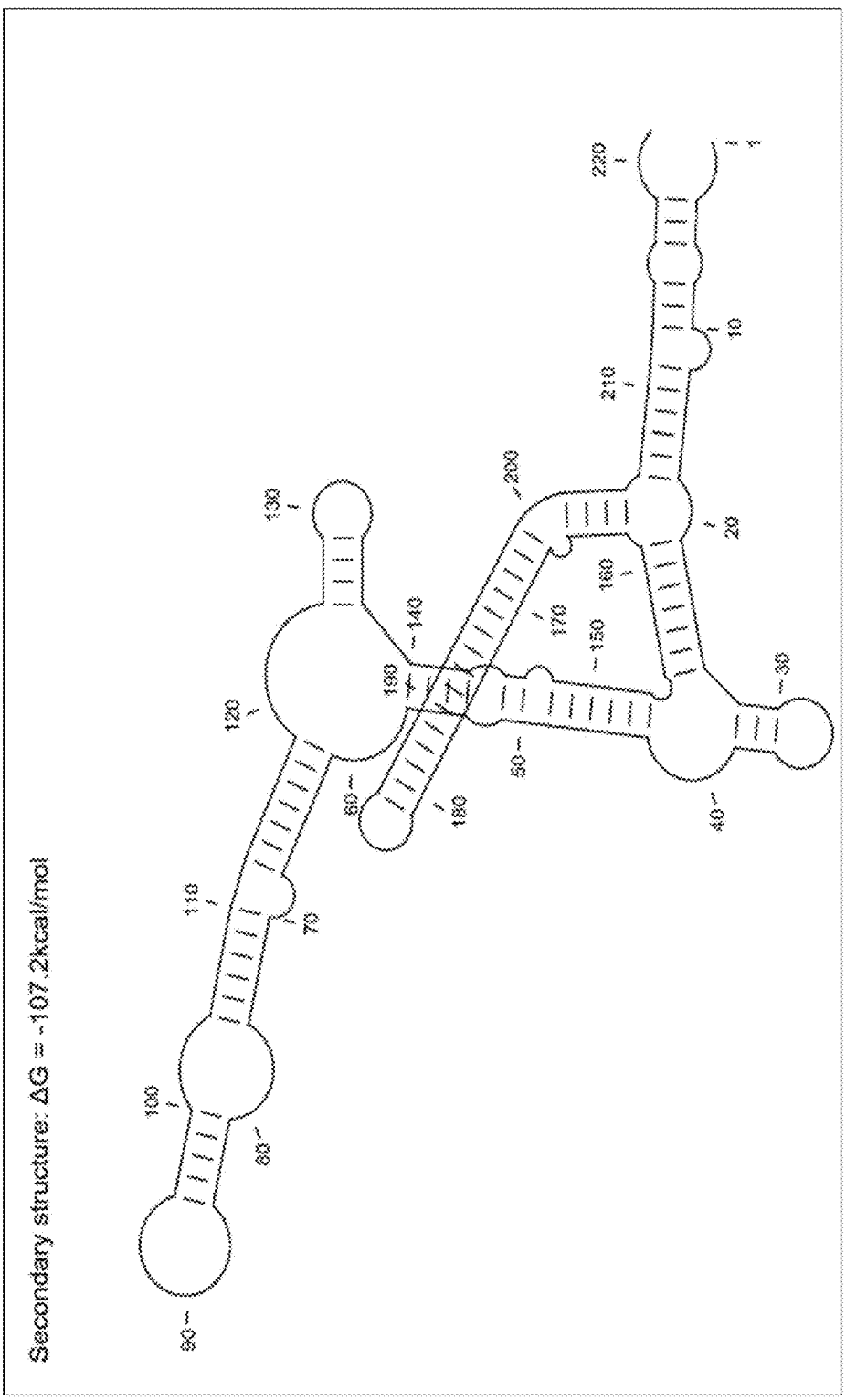
FIG. 2 shows the predicted secondary structure of the (HCV) target region in the presence of the non-extending helper oligonucleotide, showing a ΔG of −107.2 kcal/mol.

For this these HCV-positive human plasma samples, the predicted secondary structure of the HCV target region in the presence of the non-extending helper oligonucleotide is depicted in FIG. 2, showing a ΔG of −107.2 kcal/mol (CLC Genomics Workbench 6, Qiagen), and the results are shown in FIG. 1, which shows real-time PCR growth curves. As can be seen in FIG. 1, the PCR reaction is more efficient in the presence of a non-extending helper oligonucleotide than without These results demonstrate that the PCR reaction is more robust and more efficient in the presence of the non-extended helper oligonucleotide. That is, there is improved accumulation of the PCR product in the presence of the non-extended helper oligonucleotide than without Example 2: Detection of HCV Genotype 5 by Real-Time PCR As in Example 1, RNA samples used for a real-time PCR assay, but were extracted from a different HCV-positive human plasma sample than the sample used in Example 1. As in Example, 1, reagents used include Cobas® 6800/8800 generic PCR Master Mix, with the profile and conditions for use with the Cobas® 6800/8800, and using TaqMan® detection and quantitation technology. In 50 µl of PCR reaction, the final concentrations were as follows: forward and reverse primers ranged from 0.2-0.5 µM; non-extending helper oligonucleotide was at 0.20 µM; and probe was at 0.12 µM. It is believed that the forward primer, reverse primers, and non-extending helper oligonucleotides at a concentration within a range of 0.10 µM-0.50 µM would be effective.

To demonstrate the effect of the non-extending helper oligonucleotide, a real-time PCR assay using HCV-positive human plasma samples (different from the samples employed in Example 1) was conducted in duplicate with the following two experimental conditions: (1) real-time PCR with primer pairs and probe only (i.e., without non-extending helper oligonucleotide); and (2) real-time PCR with primer pairs, non-extending helper oligonucleotide, and probe. The oligonucleotides specific for HCV Genotype 5 used for the real-time PCR assay were SEQ ID NO:1 for the forward primer, SEQ ID NOs:2 and 3 for the reverse primers, SEQ ID NO:5 for the non-extending helper oligonucleotide, and SEQ ID NO:4 for the probe. As in Example 1, the non-extending helper oligonucleotide (SEQ ID NO:5) is a 53 base pair unlabeled oligonucleotide with a poly(A) tail at its 3'-end and is designed in the reverse primer binding core region of the HCV genome.

Figure 3:
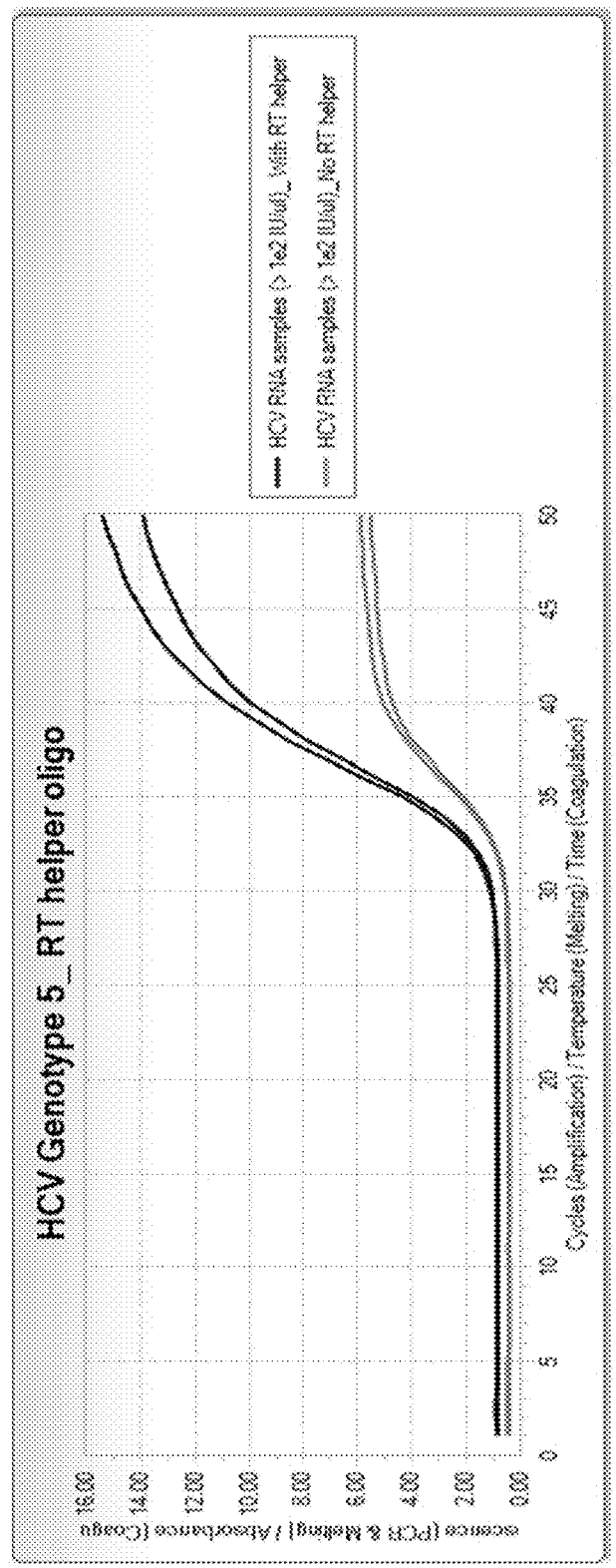
FIG. 3 shows real-time PCR growth curves of an experiment showing the primers, probes, and non-extending helper oligonucleotides and probes specific for a target nucleic acid (of HCV).
Figure 4:
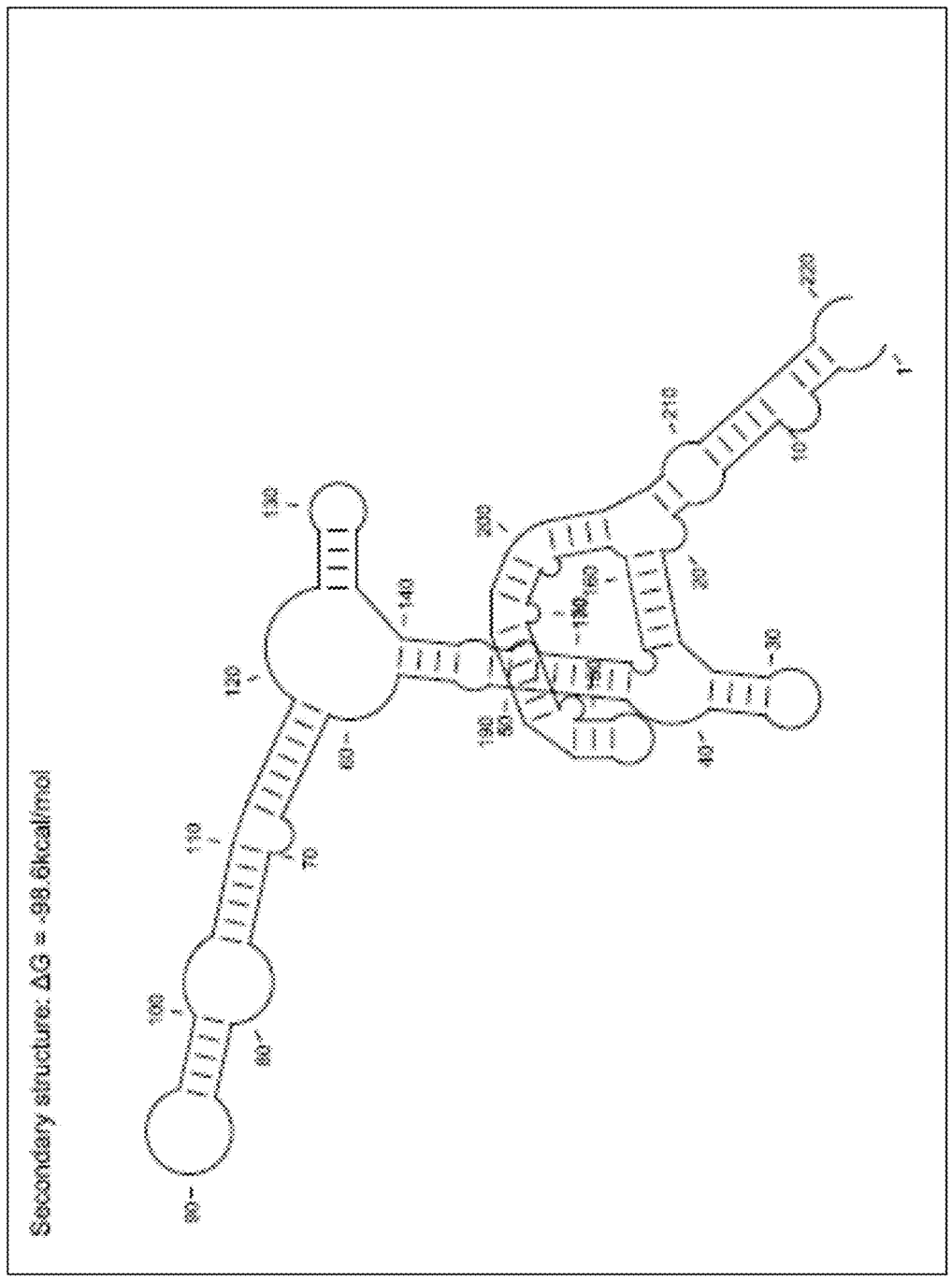
FIG. 4 shows the predicted secondary structure of the (HCV) target region in the presence of the non-extending helper oligonucleotide, showing a ΔG of −98.6 kcal/mol.

For this particular HCV-positive human plasma sample, the predicted secondary structure of the HCV target region in the presence of the non-extending helper oligonucleotide is depicted in FIG. 4, showing a ΔG of −98.6 kcal/mol and the results are shown in FIG. 3, which shows real-time PCR growth curves. As can be seen in FIG. 3, the PCR reaction is more efficient in the presence of a non-extending helper oligonucleotide than without.

These results demonstrate that the PCR reaction is more robust and more efficient in the presence of the non-extended helper oligonucleotide. That is, there is improved accumulation of the PCR product in the presence of the non-extended helper oligonucleotide than without.

Taken together, these two examples demonstrate that in different samples, the non-extending helper oligonucleotide of the present invention appears to lower the Gibbs Free Energy of the secondary structure of the target nucleic acid, which facilitates access of the target nucleic acid to the primers. This results in an improvement in amplification efficiency. Thus, the non-extending helper oligonucleotide increases the sensitivity of an amplification assay.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for detecting and/or quantitating a target nucleic acid of Hepatitis C Virus (HCV) Genotype 5 in a sample comprising:
  (a) contacting nucleic acids in the sample with amplification reagents, the amplification reagents comprising:
    at least an enzyme comprising DNA polymerase activity;
    at least nucleoside triphosphate monomers or other nucleoside monomers;
    at least one forward primer specific for the target nucleic acid, wherein the at least one forward primer comprises the sequence of SEQ ID NO:1, and at least one reverse primer specific for the target nucleic acid, wherein the at least one reverse primer comprises the sequence selected from a group consisting of SEQ ID NOs:2 and 3, for generating at least one amplicon;
    at least one non-extending helper oligonucleotide, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and
    at least one detectable probe specific for the amplicon or at least one DNA binding dye, wherein the at least one detectable probe comprises the sequence of SEQ ID NO:4;
  (b) incubating the nucleic acids with the amplification reagents for a period of time and under conditions sufficient for an amplification reaction to occur; and
  (c) detecting the amplicon with the at least one detectable probe or the at least one DNA binding dye.

2. The method of claim 1, wherein the at least one non-extending helper oligonucleotide comprises a poly(A) sequence at the 3'-end of the at least one non-extending helper oligonucleotide.

3. The method of claim 2, wherein the poly(A) sequence is between 4-12 nucleotides in length.

4. The method of claim 3, wherein the at least one non-extending helper oligonucleotide comprises the sequence of SEQ ID NO:5.

5. A kit for amplifying and detecting and/or quantitating a target nucleic acid of HCV Genotype 5 in a sample comprising amplification reagents, the amplification reagents comprising:

(a) an enzyme comprising DNA polymerase activity;
  (b) nucleoside triphosphate monomers or other nucleoside monomers;
  (c) at least one forward primer and at least one reverse primer specific for the target nucleic acid;
  (d) at least one non-extending helper oligonucleotide comprising the sequence of SEQ ID NO:5, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and
  (e) at least one detectable probe for the target nucleic acid or a DNA binding dye wherein the at least one forward primer comprises the sequence of SEQ ID NO:1;
  the at least one reverse primer comprises the sequence selected from a group consisting of SEQ ID NOs:2 and 3; and the at least one probe comprises the sequence of SEQ ID NO:4.

6. A reaction mixture effective to amplify and detect and/or quantitate a target nucleic acid in a sample comprising amplification reagents comprising:
  (a) a sample;
  (b) an enzyme comprising DNA polymerase activity;
  (c) nucleoside triphosphate monomers or other nucleoside monomers;
  (d) at least one forward primer and at least one reverse primer specific for the target nucleic acid;
  (e) at least one non-extending helper oligonucleotide comprising the sequence of SEQ ID NO:5, wherein: (i) the non-extending helper oligonucleotide does not extend, (ii) the non-extending helper oligonucleotide anneals to part of the same portion of the target nucleic acid as at least one of the primers, and (iii) the non-extending helper oligonucleotide enhances the activity of at least one of the primers; and
  (f) at least one detectable probe for the target nucleic acid or a DNA binding dye wherein the at least one forward primer comprises the sequence of SEQ ID NO:1;
  the at least one reverse primer comprises the sequence selected from a group consisting of SEQ ID NOs:2 and 3; and the at least one probe comprises the sequence of SEQ ID NO:4.

* * * * *